United States Patent
Patel

(10) Patent No.: US 10,905,677 B2
(45) Date of Patent: Feb. 2, 2021

(54) BENDAMUSTINE SOLUTION FORMULATIONS

(71) Applicant: Mahendra R. Patel, Delray Beach, FL (US)

(72) Inventor: Mahendra R. Patel, Delray Beach, FL (US)

(73) Assignee: Navinta, LLC, Ewing, NJ (US)

( * ) Notice: Subject to any disclaimer, the term of this patent is extended or adjusted under 35 U.S.C. 154(b) by 0 days.

(21) Appl. No.: 15/689,895

(22) Filed: Aug. 29, 2017

(65) Prior Publication Data

US 2018/0055823 A1 Mar. 1, 2018

Related U.S. Application Data

(60) Provisional application No. 62/465,918, filed on Mar. 2, 2017, provisional application No. 62/381,906, filed on Aug. 31, 2016.

(51) Int. Cl.
| | | |
|---|---|---|
| *A61K 31/4184* | (2006.01) | |
| *A61P 35/02* | (2006.01) | |
| *A61K 9/00* | (2006.01) | |
| *A61P 35/00* | (2006.01) | |
| *A61K 9/08* | (2006.01) | |
| *A61K 47/18* | (2017.01) | |

(52) U.S. Cl.
CPC ........ *A61K 31/4184* (2013.01); *A61K 9/0019* (2013.01); *A61K 9/08* (2013.01); *A61K 47/18* (2013.01); *A61P 35/00* (2018.01); *A61P 35/02* (2018.01)

(58) Field of Classification Search
CPC ....... A61K 31/4184; A61K 47/18; A61K 9/08
See application file for complete search history.

(56) References Cited

U.S. PATENT DOCUMENTS

| | | | |
|---|---|---|---|
| 8,344,006 B2 * | 1/2013 | Drager ..................... | A61K 9/08 514/359 |
| 8,436,190 B2 | 5/2013 | Brittain et al. | |
| 8,445,524 B2 | 5/2013 | Courvoisier et al. | |
| 8,461,350 B2 | 6/2013 | Brittain et al. | |
| 8,609,707 B2 | 12/2013 | Palepu et al. | |
| 8,609,863 B2 | 12/2013 | Brittain et al. | |
| 8,669,279 B2 | 3/2014 | Cooper et al. | |
| 8,791,270 B2 | 7/2014 | Brittain et al. | |
| 8,883,836 B2 | 11/2014 | Cooper et al. | |
| 8,895,756 B2 | 11/2014 | Brittain et al. | |
| 9,000,021 B2 | 4/2015 | Sundaram et al. | |
| 9,034,908 B2 | 5/2015 | Sundaram | |
| 9,144,568 B1 | 9/2015 | Sundaram | |
| 9,265,831 B2 | 2/2016 | Palepu et al. | |
| 9,533,955 B2 | 1/2017 | Cooper et al. | |
| 9,572,796 B2 | 2/2017 | Palepu et al. | |
| 9,572,797 B2 | 2/2017 | Palepu et al. | |
| 9,572,887 B2 | 2/2017 | Sundaram | |
| 9,579,384 B2 | 2/2017 | Sundaram et al. | |
| 9,597,397 B2 | 3/2017 | Sundaram | |
| 9,597,398 B2 | 3/2017 | Sundaram | |
| 9,597,399 B2 | 3/2017 | Sundaram | |
| 9,603,930 B2 * | 3/2017 | Patel ....................... | A61K 47/20 |
| 2013/0041004 A1 | 2/2013 | Drager et al. | |
| 2013/0210878 A1 * | 8/2013 | Soppimath ............. | A61K 47/02 514/394 |
| 2013/0210879 A1 | 8/2013 | Palepu et al. | |
| 2014/0024691 A1 * | 1/2014 | Palepu ............... | A61K 31/4184 514/394 |
| 2015/0087681 A1 | 3/2015 | Patel et al. | |
| 2015/0175554 A1 * | 6/2015 | Shrawat ............... | C07D 235/16 548/310.1 |
| 2016/0158362 A1 | 6/2016 | Patel | |

FOREIGN PATENT DOCUMENTS

| | | |
|---|---|---|
| DE | 159289 A1 | 3/1983 |
| DE | 159877 A1 | 4/1983 |
| WO | 2014127802 A1 | 8/2014 |
| WO | 2015054550 A1 | 4/2015 |
| WO | WO-2015054550 A1 * | 4/2015 |

OTHER PUBLICATIONS

Bendeka (bendamustine hydrochloride) injection, for intravenous use Initial U.S. Approval: 2008, 24 pages.

R.J.Sengwa, et. al, "Dielectric properties and hydrogen bonding interaction behavior in binary mixtures of glycerol with amides and amines", Fluid Phase Equilibria 266, (2008) 54-58.

Florence Mottu, et. al., "Organic solvents for pharmaceutical parenterals and embolic liquids: A review of toxicity data", PDA Journal of Pharmaceutical Science and Technology. Nov.-Dec. 2000;54(6):456-69. (1 page abstract only).

Package insert for TREANDA® (Bendamustine hydrochloride) injection, for intravenous infustion. 6 pages.

Ribomustine® Bendamustine HCl product monograph, updated on Jan. 2002, http://www.ribosepharm.de/pdf/ribomustin_bendamustin/productmonograph.pdf. (30 page pdf. submitted).

Cezary M. Kinart, Wojciech J. Kinart, Adam Bald & Adam Szejgis (1995): Study of the Intermolecular Interactions in Liquid N,N-Dimethylacetamide-Water Mixtures, Physics and Chemistry of Liquids: An International Journal, 30:3, 151-157.

(Continued)

*Primary Examiner* — Jean P Cornet
(74) *Attorney, Agent, or Firm* — St. Onge Steward Johnston & Reens LLC

(57) ABSTRACT

Liquid pharmaceutical formulation of Bendamustine that include bendamustine active pharmaceutical ingredient, N,N-Dimethylacetamide, and water in an amount of about 0.3% to 40%. The active pharmaceutical ingredient is Bendamustine, a pharmaceutically acceptable salt, and/or a hydrate form thereof, preferably Bendamustine HCl monohydrate. The formulations contain 20-200 mg/mL Bendamustine. The formulations are stable upon long term storage at refrigerated conditions. They can be administered to treat neoplastic conditions without reconstituting prior to administration.

11 Claims, No Drawings

(56) References Cited

OTHER PUBLICATIONS

TREANDA® (bendamustine hydrochloride) injection, for intravenous use TREANDA® (bendamustine hydrochloride) for injection, for intravenous use Initial U.S. Approval: 2008, 20 pages.
European Patent Office, Search Report and Written Opinion for Application No. 17847529.9 (Year: 2019).

* cited by examiner

BENDAMUSTINE SOLUTION FORMULATIONS

FIELD OF THE INVENTION

The present invention relates to stable liquid pharmaceutical formulations prepared from Bendamustine hydrochloride monohydrate and methods of making formulations thereof with solvents, which may optionally contain water. The present invention also relates to methods of using the liquid bendamustine formulation for the treatment of cancer.

BACKGROUND OF THE INVENTION

Bendamustine (Formula I) was initially synthesized in 1963 in the German Democratic Republic and was available under the name 'Cytostasan'.

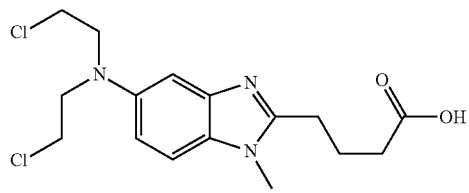

Formula I

Historically, Bendamustine was formulated as a lyophilized powder for injection. The vials are reconstituted with water at the time of patient administration. The aqueous solution is not particularly stable and must be used within 30 min after reconstitution. Some of the main degradation impurities of Bendamustine are the monohydroxy compound (Structure II) and dihydroxy compound (Structure III) as well as dimer (Structure IV) in some instances.

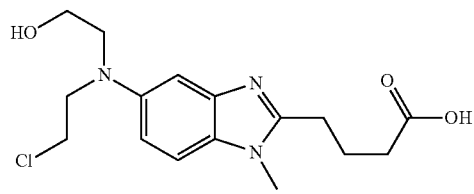

Formula II

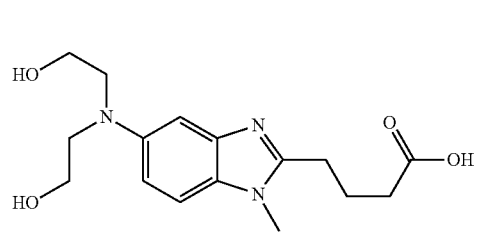

Formula III

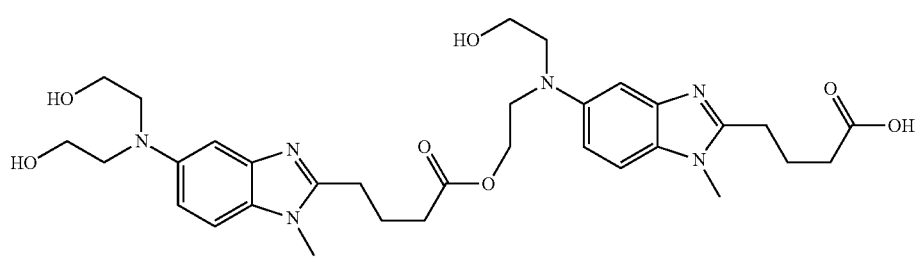

Formula IV

Bendamustine is used in the treatment of a number of cancers including leukemia, Hodgkins disease and multiple myeloma. Bendamustine is the active ingredient of the commercial product Treanda®, a lyophilized powder for reconstitution. The Treanda® product is supplied as a sterile non-pyrogenic lyophilized powder in a single-use sealed vial (e.g., 25-mg vial or 100-mg vial). Each 25-mg vial contains 25 mg of bendamustine hydrochloride and 42.5 mg of mannitol, USP. Each 100-mg vial contains 100 mg of bendamustine hydrochloride and 170 mg of mannitol, USP. The lyophilized powder is reconstituted just before its use with sterile water for injection. If particulate matter is observed after reconstitution then the injection is useless and is discarded. Lyophilized Bendamustine is also known in the art, as disclosed in e.g., U.S. Pat. Nos. 8,436,190 and 8,461,350.

Treanda® is also available as an IV solution 45 MG/0.5 ML and 18 0MG/2 ML intended for intravenous infusion only after dilution with either 0.9% Sodium Chloride Injection, USP, or 2.5% Dextrose/0.45% Sodium Chloride Injection, USP. It is supplied as a sterile clear colorless to yellow solution in a single-dose vial at the concentration of 90 mg/mL of bendamustine HCl. Each 0.5 mL vial contains 45 mg of bendamustine hydrochloride, 162 mg of Propylene Glycol, USP and 293 mg of N,N-Dimethylacetamide, EP. Each 2 mL vial contains 180 mg of bendamustine hydrochloride, 648 mg of Propylene Glycol, USP and 1172 mg of N,N-Dimethylacetamide, EP. An overfill of 0.2 mL is included in each vial.

More recently a liquid formulation of Bendamustine in a mixture of polyethylene glycol and propylene glycol has become commercially available and sold under the brand name Bendeka™. The Bendeka™ product is a 25 mg/ml solution of Bendamustine hydrochloride which needs to be diluted with water before use. Each milliliter contains 25 mg of bendamustine hydrochloride, 0.1 mL of Propylene Glycol, USP, 5 mg of Monothioglycerol, NF, in Polyethylene Glycol 400, NF. Sodium hydroxide may be used to adjust the acidity of polyethylene glycol 400. It is commercially distributed by Teva Pharmaceuticals USA as 100 MG/4 ML solution in 5 mL clear multiple-dose vials.

Since Bendamustine quickly degrades in aqueous solution, both the Treanda® and Bendeka™ products are prepared under anhydrous conditions by using an anhydrous form of bendamustine or bendamustine salt and anhydrous solvent(s). But solid anhydrous Bendamustine Hydrochloride is pharmaceutically unstable, as disclosed in U.S. Pat. No. 8,669,279. Thus, use of anhydrous Bendamustine hydrochloride in formulation requires special handling during storage and manufacturing operations.

There have been many efforts in the prior art trying to prepare stabilized bendamustine solution.

For example, solutions of bendamustine HCl in water free Propylene Glycol in presence of inert gas have been reported in German Patent No. 159289. It was also reported that the solution had reasonable stability. German Patent No. 159289 discloses details of an injectable solution of bendamustine. German Patent No. 159877 (DE) discloses a method for preparing 4-[1-methyl-5-bis(2-chloroethyl)amino-benzimidazolyl-2)-butyric acid.

Ribomustin® Bendamustine HCl product monograph, updated on January 2002, http://www.ribosepharm.de/pdf/ribomustin_bendamustin/productmonograph.pdf, provides information on Ribomustin®, including product description.

In U.S. Pat. No. 8,344,006, a Bendamustine HCl formulation is prepared by solubilizing the drug in N,N-Dimethylacetamide and Propylene Glycol. It shows that a solution of Bendamustine in propylene glycol significantly degrades upon standing at room temperature but a solution in N,N-Dimethylacetamide is relatively stable. The preferred formulation uses Bendamustine HCl in 66% N, N-DMA and 34% propylene glycol. From the data presented in the patent, it may be inferred that Propylene Glycol is required to make a pharmaceutically acceptable Bendamustine solution.

Another liquid formulation of Bendamustine is disclosed in U.S. Pat. No. 8,609,707. This patent describes a Bendamustine HCl liquid formulation prepared by solubilizing the drug in Polyethylene Glycol and Propylene Glycol. The patent discloses that the stability of the resulting formulation is improved by adding an antioxidant.

Bendamustine is poorly soluble in Polyethylene Glycol alone. There is also a risk of freezing and precipitation of the drug product at or below room temperature because the melting point of Polyethylene Glycol is near room temperature. Therefore, a small amount of Propylene Glycol is required to mitigate the issue. The resulting formulation is limited by the low solubility of the drug in the solvent mixture. Higher concentration of Propylene Glycol would improve the solubility at the expense of formulation stability and therefore this approach is not desirable.

Both the solution formulations in U.S. Pat. Nos. 8,344,006 and 8,609,707 require the use of propylene glycol. Both of the patents require strictly anhydrous conditions to avoid degradation of the drug. Accordingly, an anhydrous form of bendamustine HCl is required for the formulation. However, even with the non-aqueous formulations, significant degradation was observed from the reaction between the drug and solvent molecules. One or two glycol esters of bendamustine are formed during storage of the formulations. U.S. Patent Application Publication No. 20130210879 discloses typical impurities formed from a mixture of propylene glycol and bendamustine.

U.S. Patent Application Publication No. 20130041004 discloses a non-aqueous liquid bendamustine formulation wherein the solvent system comprises of a polar aprotic solvent DMA and a polar protic solvent selected from alcohol, propylene glycol or glycerin, and antioxidant, wherein the solvent system may contain up to 34% of propylene glycol.

U.S. Patent Application Publication No. 20160158362 discloses a bendamustine composition in which bendamustine is stabilized in a solvent system comprising DMA and glycerin, wherein glycerin takes about 5% v/v to about 60% v/v. One advantage of this bendamustine composition is that it can tolerate the water molecules in the hydrate form of a bendamustine or its salt and may contain additional (up to 1%) of water while maintaining a stable bendamustine formulation.

There exists a need for concentrated and stable liquid bendamustine formulations that have better stability and improved impurity profile and ease of use than the previously disclosed formulations. It is desired to provide a stable liquid bendamustine product which reasonably tolerates a small amount of moisture or water content. It is also desired that the liquid bendamustine product can be easily manufactured by using a readily available and stable hydrate form of bendamustine or its salt. It is further desired that the liquid bendamustine product utilizes a simple solvent system, for example, by using a single solvent, to provide liquid bendamustine products with good stability.

SUMMARY OF THE INVENTION

To achieve at least some of the foregoing objectives, the present invention provides stable bendamustine-containing liquid formulations, preferably where bendamustine may be derived from one of the hydrated forms of the pharmaceutically acceptable salt, most preferably by using a monohydrate form of Bendamustine Hydrochloride suitable for pharmaceutical use.

The present invention further provides methods of producing such liquid bendamustine formulations. The pharmaceutical formulations can be used for any condition that is sensitive to treatment with bendamustine, such as neoplastic diseases.

In one embodiment, the invention comprises a liquid pharmaceutical formulation of Bendamustine comprising bendamustine active pharmaceutical ingredient, N,N-Dimethylacetamide, and water in an amount of about 0.3% to 40%, wherein the active pharmaceutical ingredient is Bendamustine, a pharmaceutically acceptable salt, and/or a hydrate form thereof. Unlike the prior art, the formulation does not have to be lyophilized prior to administration to a patient. Accordingly, in preferred embodiments, the bendamustine liquid pharmaceutical formulation is not lyophilized prior to administration.

In some embodiments, the formulation includes water in an amount of about 1% to about 40%. In some of those embodiments, the formulation includes water in an amount of about 1% to about 30%. In some preferred embodiments, the formulation includes 1% to 10% water. In certain preferred embodiments, the formulation includes water in an amount of about 20%.

In certain embodiments, the bendamustine active pharmaceutical ingredient is in an amount of about 20-200 mg/mL. In some of these embodiments, there is 60 to 200 mg/mL bendamustine active ingredient. In some of those embodiments, there is 80 to 180 mg/mL bendamustine active ingredient. In other preferable embodiments, there is 90 to 200 mg/mL bendamustine active ingredient.

In certain preferred embodiments, the bendamustine active pharmaceutical ingredient is in the form of Bendamustine HCl monohydrate.

In some embodiments, no solvent derived ester impurities are produced when the formulation is stored under a refrigerated condition for an extended period of time. In some of those embodiments, no solvent derived ester impurities are produced after 3 months storage of the formulation at 5° C. In some of those embodiments, no solvent derived impurities are produced after 6 months storage of the formulation at 5° C. In certain of those embodiments, no solvent derived impurities are produced after 9 months storage of the formulation at 5° C. In some preferred embodiments, no solvent derived impurities are produced after one year storage of the formulation at refrigerated conditions.

In certain of embodiments, the formulation produces less than 0.2% deschloroethyl bendamustine after 3 months storage of the formulation at 5° C. In some of those embodiments, the formulation produces less than 0.1% deschloroethyl bendamustine. In certain of those embodiments, the formulation produces less than 0.05% deschloroethyl bendamustine after 3 months storage of the formulation at 5° C.

In some embodiments, the formulation contains not more than 2% of bendamustine monohydroxy impurity when the formulation is stored under a refrigerated condition for an extended period of time. In some of those embodiments, the formulation produces less than 0.5% monohydroxy bendamustine after 3 months storage of the formulation at 5° C. In certain of those embodiments, the formulation produces less than 0.1% monohydroxy bendamustine. In certain of those embodiments, the formulation produces less than 0.05% monohydroxy bendamustine after 3 months storage of the formulation at 5° C.

In certain embodiments, the liquid bendamustine formulation contains not more than about 2% bendamustine polar impurity when the formulation stored under a refrigerated condition for an extended period of time.

In some embodiments, the total concentration of all bendamustine impurities in the final product is less than about 4.0% when the formulation is stored under refrigerated storage conditions for an extended period of time. In some of those embodiments, the formulation produces less than 0.75% total impurities after 3 months storage of the formulation at 5° C. In certain of those embodiments, the formulation produces less than 0.2% total impurities. In certain preferred embodiments, the formulation produces less than 0.1% total impurities after 3 months storage of the formulation at 5° C.

In certain of embodiments, the formulation produces less than 0.2% deschloroethyl bendamustine after 6 months storage of the formulation at 5° C. In some of those embodiments, the formulation produces less than 0.1% deschloroethyl bendamustine. In certain of those embodiments, the formulation produces less than 0.05% deschloroethyl bendamustine after 6 months storage of the formulation at 5° C.

In some embodiments, the formulation produces less than 0.5% Monohydroxy bendamustine after 6 months storage of the formulation at 5° C. In certain of those embodiments, the formulation produces less than 0.1% Monohydroxy bendamustine. In certain of those embodiments, the formulation produces less than 0.05% Monohydroxy bendamustine after 6 months storage of the formulation at 5° C.

In certain embodiments, the formulation produces less than 0.75% total impurities after 6 months storage of the formulation at 5° C. In certain of those embodiments, the formulation produces less than 0.2% total impurities. In certain preferred embodiments, the formulation produces less than 0.1% total impurities after 6 months storage of the formulation at 5° C.

In some embodiments, the formulation produces less than 0.2% deschloroethyl bendamustine after 9 months storage of the formulation at 5° C. In some of those embodiments, the formulation produces less than 0.1% deschloroethyl bendamustine. In certain of those embodiments, the formulation produces less than 0.05% deschloroethyl bendamustine after 9 months storage of the formulation at 5° C.

In some embodiments, the formulation produces less than 0.5% Monohydroxy bendamustine after 9 months storage of the formulation at 5° C. In certain of those embodiments, the formulation produces less than 0.1% Monohydroxy bendamustine. In certain of those embodiments, the formulation produces less than 0.05% Monohydroxy bendamustine after 9 months storage of the formulation at 5° C.

In some embodiments, the formulation produces less than 1.0% total impurities after 9 months storage of the formulation at 5° C. In certain of those embodiments, the formulation produces less than 0.5% total impurities. In certain preferred embodiments, the formulation produces less than 0.2% total impurities after 9 months storage of the formulation at 5° C.

In some embodiments, the formulation produces less than 0.2% deschloroethyl bendamustine after 12 months storage of the formulation at 5° C. In some of those embodiments, the formulation produces less than 0.1% deschloroethyl bendamustine. In certain of those embodiments, the formulation produces less than 0.05% deschloroethyl bendamustine after 12 months storage of the formulation at 5° C.

In some embodiments, the formulation produces less than 0.5% Monohydroxy bendamustine after 12 months storage of the formulation at 5° C. In certain of those embodiments, the formulation produces less than 0.1% Monohydroxy bendamustine. In certain of those embodiments, the formulation produces less than or equal to 0.05% Monohydroxy bendamustine after 12 months storage of the formulation at 5° C.

In some embodiments, the formulation produces less than 1.0% total impurities after 12 months storage of the formulation at 5° C. In certain of those embodiments, the formulation produces less than 0.5% total impurities. In certain preferred embodiments, the formulation produces less than 0.2% total impurities after 12 months storage of the formulation at 5° C.

In certain embodiments, the formulation produces not more than 2% of bendamustine monohydroxyl impurity when stored under a refrigerated condition for a year.

The some embodiments, the formulation produces not more than 2% bendamustine polar impurity when stored under refrigerated conditions for a year.

In certain embodiments, the total concentration of all bendamustine impurities in the final product is less than about 4.0% under refrigerated storage conditions for a year.

In another embodiment, the invention also comprises a liquid pharmaceutical formulation of Bendamustine consisting of about 20-200 mg/mL a bendamustine active pharmaceutical ingredient, N,N-Dimethylacetamide, and about 1% to about 30% water; wherein the active pharmaceutical ingredient is Bendamustine, a pharmaceutically acceptable salt, and/or a hydrate form thereof. In certain of those embodiments, the bendamustine active pharmaceutical ingredient is in an amount of about 90-200 mg/mL. In some preferred embodiments, the bendamustine active pharmaceutical ingredient is in the form of Bendamustine HCl monohydrate. The formulation is stable when stored under refrigerated conditions for an extended period of time.

In yet another embodiment, the invention comprises a liquid pharmaceutical formulation of Bendamustine consisting of a bendamustine active pharmaceutical ingredient, N,N-Dimethylacetamide, and up to about 10% water; wherein the active pharmaceutical ingredient is Bendamustine, a pharmaceutically acceptable salt, and/or a hydrate form thereof. In preferred embodiments, the formulation comprises about 1.0% to 10% water, more preferably about 1.0% to about 5.0%.

In a further embodiment, the invention comprises a method of treating a neoplastic disease by diluting the inventive bendamustine formulations, and administering an effective amount of said diluted formulation to a mammal in need thereof. The bendamustine does not need to be reconstituted during the step of diluting. In preferred embodiments, the method is used to treat leukemia or Hodgkin's disease.

In some preferred embodiments, the invention comprises a method of treating a neoplastic disease by diluting a formulation comprising about 90-200 mg/mL bendamustine HCl monohydrate, N,N-Dimethylacetamide, and about 1% to about 30% water; and administering an effective amount of said diluted formulation to a mammal in need thereof. The bendamustine does not need to be reconstituted during the step of diluting.

DETAILED DESCRIPTION OF THE INVENTION

The present invention provides liquid pharmaceutical formulation of Bendamustine comprising bendamustine active pharmaceutical ingredient, N,N-Dimethylacetamide, and water in an amount of about 0.3% to 40%. The source of bendamustine in the formulation may be bendamustine free base, its pharmaceutically acceptable salts, and/or various hydrate forms. Preferably, the pharmaceutical composition includes bendamustine hydrochloride. More preferably, the pharmaceutical composition includes bendamustine hydrochloride monohydrate.

Compared to anhydrous bendamustine hydrochloride, bendamustine hydrochloride monohydrate is a better choice to be used in the preparation of bendamustine liquid formulations. As stated previously, anhydrous bendamustine HCl is unstable and may convert to hydrates upon storage in a solid form. In contrast, bendamustine hydrochloride monohydrate has a better impurity profile than anhydrous bendamustine hydrochloride and is more readily accessible in pure form (e.g., without residual solvents). Bendamustine hydrochloride monohydrate may be used directly to prepare a ready for use or ready for further dilution pharmaceutical formulation without the need to lyophilize bendamustine HCl prior to the formulation.

The liquid bendamustine formulations of the present invention have a high concentration of the drug (i.e., bendamustine, its salt and/or hydrate thereof) with very good stability and improved impurity profile. The novel liquid bendamustine formulations of the present invention may also be easily prepared by a simple process.

Aqueous solutions of Bendamustine are not very stable and all the prior work in making a solution formulation of Bendamustine was aimed at using non aqueous solvents where Bendamustine dissolves easily and does not generate impurities on storage. Generally, an anhydrous form of Bendamustine was used to prepare these prior art solutions.

It is reported in U.S. Pat. No. 8,344,006 that solubility of Bendamustine hydrochloride in DMA is about 56 mg/mL at room temperature. We have found that Bendamustine hydrochloride hydrate has a solubility of about 65 mg/mL at 2-8° C. We observed that one can routinely make solutions of Bendamustine hydrochloride monohydrate in DMA containing up to 10% water with drug concentrations up to about 200 mg/mL.

A solution of 90 mg/mL of Bendamustine hydrochloride hydrate in DMA did not develop any precipitate when stored at 2-8° C. for five months. Surprisingly, a solution which contains about 0.5% water was stable at 5° C. up to 3 months with less than 2% degradation. Subsequently, we found that solutions of Bendamustine hydrochloride hydrate in DMA containing up to about 40% water are stable for up to 9 months at 5° C. These observations allowed us to prepare pharmaceutical dosing solutions of Bendamustine hydrochloride hydrate in DMA with or without additional water.

All % of solvents herein refer to volume %, unless otherwise specified. The term "% v/v" (also written as "v/v %") means the volume of a solute in the total volume of solution. As one skilled in the art would understand, when the solute is a liquid, sometimes it is convenient to express its concentration in volume/volume percent. The calculation of "% v/v" is:

Concentration solute (v/v %)=volume solute (mL)
Total volume of solution (mL)×100

As used herein, the term "about" is defined as ±10%, preferably ±5%.

Solutions of Bendamustine in N, N Dimethylacetamide with up to about 40% water provide superior drug solubility and stability of Bendamustine in the resulting solution. Without wishing to be bound by theory, it is believed that the reason for less reactivity and hence the stability of Bendamustine solution in DMA, even in presence of water, is due to significant hydrogen bonding in solution. It has been reported that a stable hydrogen bonded complex is formed between one molecule of DMA and two molecules of water. This mole ratio of DMA and water corresponds to 29% water by weight based on the total weight of water and DMA. It is believed that the hydrogen bonding between DMA, bendamustine and water could be responsible for better stability of the formulation. As a result, the formulation of the present invention can even tolerate the presence of up to about 40% water. In some embodiments, it tolerates about 10% of water; in other embodiments, it tolerates about 20% of water; in further additional embodiments, it tolerates about 25% of water. In some other embodiments, it tolerates about 25% to about 40% of water.

The present formulations do not require glycerin and/or an antioxidant and are able to achieve greater solubility than previous formulations containing DMA, glycerin and/or antioxidant.

Based on an actual or calculated weight of bendamustine free base in the pharmaceutical formulation (regardless whether the source of bendamustine is a bendamustine salt and/or hydrate form), the active pharmaceutical ingredient (i.e., Bendamustine, a pharmaceutically acceptable salt, and/or a hydrate form thereof) is in an amount of about 20 to about 200 mg/mL; preferably, in an amount of about 40 to 200 mg/mL; more preferably, in an amount of about 60 to 180 mg/mL; even more preferably, in an amount of about 60 to 150 mg/mL.

Analysis of the liquid formulations of the present invention can be performed using techniques known in the art, including, for example, HPLC, gas chromatography, and NMR. After exposure to typical commercial storage conditions, analysis of the formulations of the present invention will indicate that the formulation contains no less than about 90% of the amount of bendamustine present prior to exposure to the storage conditions. Preferably, analysis will indicate that the formulation contains no less than about 95% of the amount of bendamustine present prior to exposure to the storage conditions. More preferably, analysis will indicate that the formulation contains no less than about 98% of the amount of bendamustine prior to exposure to the storage conditions.

Storage conditions refers to those long term, intermediate and accelerated conditions discussed in ICH guidelines for stability testing of active pharmaceutical ingredients and finished pharmaceutical products (WHO 2009), the contents of which is incorporated herein by reference. Namely, storage conditions include 5° C.±3° C., 25° C.±2° C./60% RH±5% RH, 30° C.±2° C./65% RH±5% RH, and 40° C.±2° C./75% RH±5% RH. As used herein, storage of compositions refers to storage within a container closure system.

In preferred embodiments of the present invention, analysis of the formulations of the present invention will indicate that the formulation contains no less than about 90% of the amount of bendamustine present prior to exposure to storage conditions that include temperatures of about 5° C. and time periods of about 30 days (about 1 month) to about 365 days (about 1 year). Preferably, analysis of the formulations of the present invention will indicate that the formulation contains no less than about 90% of the amount of bendamustine present prior to exposure to storage conditions that include temperatures of about 5° C. and time periods of about 30 days (about 1 month), about 90 days (about 3 months), about 180 days (about 6 months), and about 240 days (about 9 months). Preferably, analysis will indicate that the formulation contains no less than about 95% of the amount of bendamustine present prior to exposure to storage conditions that include temperatures of about 5° C. and time periods of about 30 days (about 1 month) to about 365 days (about 1 year). More preferably, analysis will indicate that the formulation contains no less than about 95% of the amount of bendamustine present prior to exposure to storage conditions that include temperatures of about 5° C. and time periods of about 30 days (about 1 month), about 90 days (about 3 months), about 180 days (about 6 months), about 240 days (about 9 months), and about 365 days (about 1 year).

The solution of Bendamustine hydrochloride hydrate prepared according to this invention may be diluted or constituted with 0.9% Sodium Chloride in water, or 5% Dextrose in water to obtain a dosing solution suitable for intravenous dosing to a patient. An important advantage of this invention is that one may prepare a much higher concentration of Bendamustine in DMA than other mixed solvent systems reported in prior art. Since the drug has a higher concentration in the present invention, the patient will be exposed to less amounts of organic solvents for a given dose of the drug.

Liquid formulations of the present invention are stable over the course of a typical commercial storage period. Typical commercial storage conditions include time periods of, for example, about 30 days, about 90 days, about 180 days, and about 365 days (about 1 month, about 3 months, about 6 months, and about 1 year). Typical commercial storage conditions also include temperatures of about 25° C. (ambient room temperature) and refrigerated temperatures below ambient room temperature, for example, about 5° C. Preferably, the liquid formulations of the present invention are stored at refrigerated temperatures.

As used herein, "stable" is defined as no more than about a 10% loss of bendamustine under typical commercial storage conditions. Preferably, formulations of the present inventions will have no more than about a 10% loss of bendamustine, more preferably, no more than about a 5% loss of bendamustine, under typical commercial storage conditions. An advantage of the present formulations, is that they show improved stability over prior bendamustine formulations. That is, they show less than 2% loss of bendamustine under typical storage conditions.

Another aspect of this invention is that, in this process, Bendamustine HCl monohydrate, which is accessible in pure form without any residual solvents, can be used directly in the formulation. Another benefit is that there is no need to lyophilize Bendamustine HCl as a means of purification prior to the formulation.

Bendamustine HCl monohydrate can be prepared by the method disclosed in Journal of Practical Chemistry, 1963, 178-186, the contents of which are incorporated herein by reference. Compared to Bendamustine HCl anhydrous, the use of Bendamustine HCl monohydrate has the following advantages. Bendamustine HCl monohydrate has a better impurity profile and is more readily accessible in pure form without residual solvents. Thus it can be used directly in the formulation of a pharmaceutical composition ready for administration. Also, as noted earlier, the anhydrous Bendamustine HCl is pharmaceutically very unstable and converts to the hydrate form upon storage. The degradation of Bendamustine HCl is mainly caused by hydrolysis of the chloride of bendamustine and formation of ester from the carboxylic group of bendamustine with individual solvents. In alcoholic solvents such as methanol or ethanol, Bendamustine is easily converted to methyl or ethyl ester at room temperature. By using the preferred solvent mixture of DMA and optionally water disclosed in the present invention, only trace amounts of impurities are formed.

A further important feature of the presently disclosed formulations is they do not produce any solvent derived ester impurities. Moreover, the major degradation impurity is not a new chemical entity that requires additional safety testing. The principal impurity in certain formulations of the present invention is a known metabolite of bendamustine.

An embodiment of the invention is a pharmaceutical liquid composition of Bendamustine HCl monohydrate, preferably containing not more than 2% of Bendamustine monohydroxy impurity when stored under a refrigerated condition (2 to 8 degrees C.) for an extended period of time.

As used herein, an "extended period of time" means 9 months or greater.

Another embodiment of the invention is a liquid formulation of Bendamustine containing not more than about 2%, preferably less than 1%, of Bendamustine polar impurity when stored under refrigerated condition for an extended period of time.

A further embodiment of the invention is a process for manufacturing a liquid formulation of Bendamustine HCl that controls Bendamustine degradation impurities during the process such that the total concentration of all Bendamustine impurities in the final product is less than about 4.0% under refrigerated storage for an extended period of time.

Another embodiment of the invention is a liquid formulation of bendamustine containing not more than about 2%, preferably less than 1%, of bendamustine polar impurity when stored under refrigerated condition for an extended period of time.

EXPERIMENTS

HPLC Procedure for Analysis of Bendamustine Formulations:

Solvent A: Water:MeCN(acetonitrile):TFA (trifluoroacetic acid) (90:10:0.1)
Solvent B: Water:MeCN:TFA (50:50:0.1)
UV: 230 nm
Flow rate: 1.0 mL/min
Column: Symmetry C-18 (250×4.6 mm) 5 μm, or equivalent Column temp: 25° C.
Sample temp: 5° C.
Injection volume: 10 μL
Run time: 53 min
Diluent: Methanol
HPLC Gradient:

| Time(min.) | % A | % B |
|---|---|---|
| 0.01 | 100 | 0 |
| 18 | 50 | 50 |
| 30 | 45 | 55 |
| 40 | 35 | 65 |
| 41 | 10 | 90 |
| 43 | 100 | 0 |
| 53 | 100 | 0 |

Sample preparation: Dilute the solution with methanol to prepare a sample with concentration of 1 mg/mL for injection directly in to HPLC. It may be necessary to perform a second dilution to reach a targeted sample concentration.

Results:

Percent of each bendamustine related compound is calculated against average peak area of Bendamustine HCl low level working standard using an equation below:

$$\% \text{ impurity} = \frac{Ru}{Rs} \times \frac{\text{Standard Concentration}}{\text{Sample Concentration}} \times 100\% \times 1000$$

Where Ru is area of the impurity peak and Rs is area of the standard peak

HPLC Retention Times and Structures of Bendamustine Impurities

| Sr No | Name of Impurity | RT (min) | RRT | Structure |
|---|---|---|---|---|
| 1 | Deschloroethyl bendamustine | 13.8 | 0.55 | 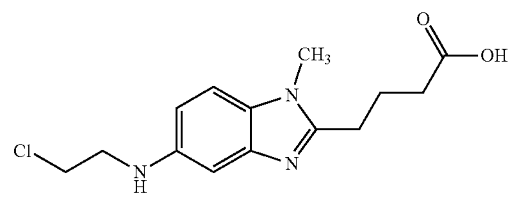 [SMILES: Cn1c(CCCC(=O)O)nc2cc(NCCCl)ccc21] |
| 2 | Monohydroxy bendamustine | 14.5 | 0.58 | 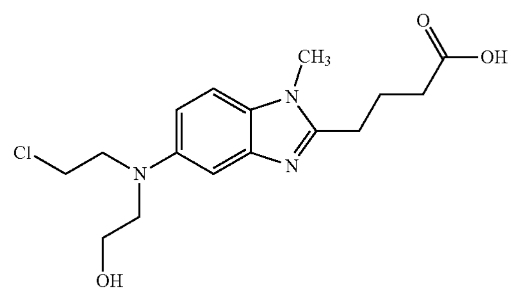 [SMILES: Cn1c(CCCC(=O)O)nc2cc(N(CCO)CCCl)ccc21] |
| 3 | Bendamustine methylester | 31 | 1.24 | 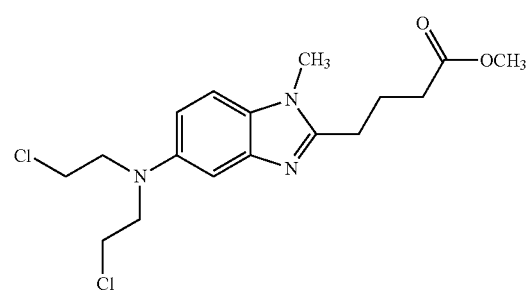 [SMILES: COC(=O)CCCc1nc2cc(N(CCCl)CCCl)ccc2n1C] |
| 4 | Bendamustine | 25 | 1.00 | 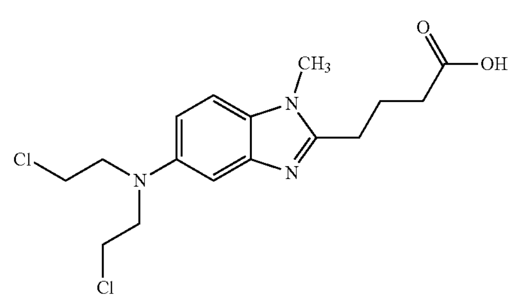 [SMILES: Cn1c(CCCC(=O)O)nc2cc(N(CCCl)CCCl)ccc21] |

EXAMPLE 1

Solubility of Bendamustine Hydrochloride in DMA-Water Mixture

To 10 ml of DMA-water mixture, excess (~2-3 g) of Bendamustine hydrochloride hydrate was added and the mixture was stirred for 24 hr while keeping in a constant temperature bath. After 24 hr, the mixture was centrifuged to remove the undissolved solid and the supernatant was filtered through a 0.2 micron filter. The clear filtrate was assayed.

Results:

| Composition | Temperature | Solubility |
| --- | --- | --- |
| DMA | 5° C. | 72 mg/mL |
| DMA:Water 97:3 | 5° C. | 116 mg/mL |
| DMA:Water 95:5 | 5° C. | 114 mg/mL |
| DMA:Water 90:10 | 5° C. | 201 mg/mL |
| DMA:Water 80:20 | 5° C. | 169 mg/mL |
| DMA:Water 60:40 | 5° C. | 67 mg/mL |

EXAMPLE 2

Preparation of Bendamustine HCl solution 90/mg/mL in DMA:water (99:1)

A mixture of 99 mL of DMA and 1 mL of water was stirred until a clear solution was formed. This solution was degassed by passing $N_2$ for 30 min. In a 100 mL volumetric flask containing 80 mL of this solution 9.46 g of Bendamustine hydrochloride hydrate was added and stirred until the solid dissolved (5-10 min). The solution was diluted to volume with additional degassed DMA-water and stirred for 5 min. The solution was filtered through a 0.2 micron filter and amber glass vials were filled with 1 ml of the filtrate. The vials were flushed with $N_2$ and sealed. The vials were kept on stability at and analyzed at various time points.

EXAMPLE 3

Preparation of Bendamustine HCl solution 90 mg/mL in DMA:water (98:2)

A solution prepared from 98 mL DMA and 2 mL water was used to make a solution of Bendamustine HCl solution 90 mg/mL as described in Example 2.

EXAMPLE 4

Preparation of Bendamustine HCl solution 90 mg/mL in DMA:water (97:3)

A solution prepared from 97 mL DMA and 3 mL water was used to make a solution of bendamustine HCl solution 90 mg/mL as described in Example 2.

EXAMPLE 5

Preparation of Bendamustine HCl solution 180 mg/mL in DMA:water (98:2)

A mixture of 98 mL of DMA and 2 mL of water was stirred until a clear solution was formed. This solution was degassed by passing N2 for 30 min. In a 100 mL volumetric flask containing 80 mL of this solution 18.43 g of Bendamustine hydrochloride hydrate was added and stirred until the solid dissolved (5-10 min). The solution was diluted to volume with additional degassed DMA-water and stirred for 5 min. The solution was filtered through a 0.2 micron filter and amber glass vials were filled with 1 ml of the filtrate. The vials were flushed with N2 and sealed. The vials were kept on stability at and analyzed at various time points.

EXAMPLE 6

Preparation of Bendamustine HCl solution 100 mg/mL in DMA:water (60:40)

Bendamustine hydrochloride, hydrate (10.457 g) was added to 50 mL of degassed DMA and the mixture was stirred for 5 min until the solid dissolved. To this solution 40 ml of purified water was added with stirring. After through mixing the solution was diluted to 100 mL by adding DMA. The solution was stirred for an additional 5 min. and the resulting 100 ml solution of 100 mg/mL of Bendamustine hydrochloride was used to fill 2 mL vials. The vials were flushed with N2, and sealed. The vials were kept on stability at various temperatures and analyzed at various time points.

Other solutions of Bendamustine hydrochloride hydrate in DMA with varying amounts of water were prepared by adjusting the quantities of DMA and water and following the procedure of example 1.

Results: stability of the solution formulations

| Formulation | Potency (mg/ml) | Stability Condition | Assay | Related Compounds (%) | | |
| --- | --- | --- | --- | --- | --- | --- |
| | | | | 0.55 RRT DCE | 0.58 RRT Monohydroxyl | Total Impurity |
| DMA: Water 99:01 | 90 | Initial | 101.3 | 0.03 | 0.03 | 0.08 |
| | | 3M@5° C. | 100.7 | 0.03 | 0.03 | 0.06 |
| | | 6M@5° C. | 100.3 | 0.03 | 0.04 | 0.08 |
| | | 9M@5° C. | 98.1 | 0.04 | 0.04 | 0.13 |
| | | 12M@5° C. | 100 | 0.02 | 0.04 | 0.06 |
| DMA: Water 98:02 | 90 | Initial | 101.1 | 0.03 | 0.02 | 0.08 |
| | | 3M@5° C. | 100.4 | 0.02 | 0.04 | 0.06 |
| | | 6M@5° C. | 99.9 | 0.03 | 0.04 | 0.08 |
| | | 9M@5° C. | 98.8 | 0.03 | 0.04 | 0.08 |
| | | 12M@5° C. | 101 | 0.02 | 0.05 | 0.07 |
| DMA: Water 97:03 | 90 | Initial | 101.8 | 0.03 | 0.03 | 0.07 |
| | | 3M@5° C. | 101.7 | 0.02 | 0.04 | 0.06 |
| | | 6M@5° C. | 100.8 | 0.02 | 0.04 | 0.07 |
| | | 9M@5° C. | 98.8 | 0.03 | 0.04 | 0.07 |
| | | 12M@5° C. | 101 | 0.02 | 0.05 | 0.07 |

-continued

| Formulation | Potency (mg/ml) | Stability Condition | Assay | Related Compounds (%) 0.55 RRT DCE | 0.58 RRT Monohydroxyl | Total Impurity |
|---|---|---|---|---|---|---|
| DMA:Water 99:01 | 180 | Initial | 99.9 | 0.03 | 0.03 | 0.06 |
|  |  | 3M@5° C. | 101.3 | 0.02 | 0.04 | 0.06 |
|  |  | 6M@5° C. | 99.3 | 0.03 | 0.04 | 0.08 |
|  |  | 9M@5° C. | 100.6 | 0.02 | 0.04 | 0.12 |
|  |  | 12M@5° C. | 100.4 | 0.03 | 0.04 | 0.08 |
| DMA:Water 98:02 | 180 | Initial | 100.6 | 0.03 | 0.03 | 0.07 |
|  |  | 3M@5° C. | 102.4 | 0.02 | 0.03 | 0.05 |
|  |  | 6M@5° C. | 100.8 | 0.02 | 0.06 | 0.06 |
|  |  | 9M@5° C. | 99.4 | 0.02 | 0.04 | 0.12 |
|  |  | 12M@5° C. | 101 | 0.03 | 0.04 | 0.08 |
| DMA:Water 97:03 | 180 | Initial | 100.7 | 0.03 | 0.03 | 0.07 |
|  |  | 3M@5° C. | 99.9 | 0.04 | 0.02 | 0.06 |
|  |  | 6M@5° C. | 99.5 | 0.03 | 0.05 | 0.09 |
|  |  | 9M@5° C. | 98.3 | 0.02 | 0.04 | 0.11 |
|  |  | 12M@5° C. | 100.2 | 0.03 | 0.05 | 0.08 |
| DMA:Water 90:10 | 200 | Initial | 100.2 | 0.03 | 0.02 | 0.07 |
|  |  | 3M@5° C. | 101.9 | 0.02 | 0.05 | 0.06 |
|  |  | 6M@5° C. | 98.1 | 0.02 | 0.05 | 0.1 |
|  |  | 9M@5° C. | 100.2 | 0.02 | 0.06 | 0.13 |
| DMA:Water 90:10 | 100 | Initial | 100.3 | 0.1 | 0.04 | 0.14 |
|  |  | 3M@5° C. | 99.8 | 0.19 | 0.04 | 0.23 |
| DMA:Water 80:20 | 100 | Initial | 99.9 | 0.03 | 0.04 | 0.07 |
|  |  | 3M@5° C. | 101.8 | 0.09 | 0.06 | 0.15 |
| DMA:Water 75:25 | 100 | Initial | 97.7 | 0.04 | 0.03 | 0.11 |
|  |  | 3M@5° C. | 99.01 | 0.11 | 0.09 | 0.20 |
| DMA:Water 60:40 | 100 | Initial | 99.1 | 0.05 | 0.09 | 0.18 |
|  |  | 3M@5° C. | 98.9 | 0.07 | 0.46 | 0.67 |

The pharmaceutical formulations can be used for any condition that is sensitive to treatment with bendamustine, such as neoplastic diseases. Accordingly, the present invention also provides a method of treating a neoplastic disease in mammals, which comprises the steps of: diluting a pharmaceutical composition of the present invention, and administering an effective amount of said diluted pharmaceutical composition to a mammal in need thereof. The neoplastic disease may be leukemia or Hodgkin's disease.

The term "effective amount," as used herein, refers to the amount determined to be required to produce the physiological effect intended and associated with a given drug, as measured according to established pharmacokinetic methods and techniques, for the given administration route. Appropriate and specific therapeutically effective amounts can be readily determined by the attending diagnostician, as one skilled in the art, by the use of conventional techniques. The effective dose will vary depending upon a number of factors, including the type and extent of progression of the disease or disorder, the overall health status of the particular patient, the relative biological efficacy of the compound selected, the formulation of the active agent with appropriate excipients, and the route of administration.

The liquid formulations of bendamustine described herein are intended to be administered via injection, for example, they may be administered subcutaneously, intracutaneously, intravenously, intramuscularly, intra-articularly, intrasynovially, intrasternally, intrathecally, intralesionally, intracranially or via infusion. In a typical preparation, the volume of the liquid formulation of the present invention needed for the required dose can be aseptically withdrawn and transferred to an infusion bag of 0.9% Sodium Chloride (or other pharmaceutically acceptable intravenous solution) for injection. After transfer, the contents of the infusion bag are thoroughly mixed. Administration by intravenous infusion is typically provided over a time period of from about 30 to about 60 minutes. Previously described lyophilized formulations of bendamustine required reconstitution of the lyophilized bendamustine prior to mixture with the acceptable intravenous solution before infusion.

It is envisioned that the pharmaceutical formulations and preparations of the present invention can be administered in combination with one or more anti-neoplastic agents where the anti-neoplastic agent is given prior to, concurrently with, or subsequent to the administration of the formulation or preparation of the present invention. Pharmaceutically acceptable anti-neoplastic agents are known in the art.

It should be noted that the invention in its broader aspects is not limited to the specific details, representative compositions, methods, and processes, and illustrative examples described in connection with the preferred embodiments and preferred methods. Modifications and equivalents will be apparent to practitioners skilled in this art and are encompassed within the spirit and scope of the appended claims.

What is claimed is:

1. A liquid pharmaceutical formulation of Bendamustine consisting essentially of: 90-200 mg/mL bendamustine active pharmaceutical ingredient,
   N,N-Dimethylacetamide and
   water in an amount of about 1% to 40% v/v,
   wherein the active pharmaceutical ingredient is Bendamustine Hydrochloride or a hydrate form thereof,
   the formulation is ready for use for up to 3 months at room temperature storage conditions without the need to lyophilize or ready for further dilution for up to 3 months at room temperature storage conditions without the need to lyophilize, and
   the formulation contains no less than about 98% of the amount of the bendamustine active pharmaceutical ingredient upon analysis by HPLC at initial testing and after 3 months at room temperature, and a ratio of N,N-Dimethylacetamide to water is in a range from about 99:1 to about 60:40.

2. The formulation of claim 1, wherein the bendamustine active pharmaceutical ingredient is in the form of Bendamustine HCl monohydrate.

3. The formulation of claim 2, wherein water is in an amount of about 1% to about 10% v/v of the formulation.

4. The formulation of claim 1, wherein no solvent derived ester impurities are produced when the formulation is stored at room temperature for 3 months.

5. The formulation of claim 1 containing not more than 2% of bendamustine monohydroxy impurity when the formulation is stored at room temperature for 3 months.

6. The formulation of claim 1 containing not more than about 2% bendamustine polar impurity when the formulation stored at room temperature for 3 months.

7. The formulation of claim 1, wherein total concentration of all bendamustine impurities is less than about 4.0% when the formulation is stored at room temperature for 3 months.

8. The formulation of claim 1, wherein the water is in an amount of about 1% to about 30% v/v of the formulation.

9. The formulation of claim 8, wherein the bendamustine active pharmaceutical ingredient is in the form of Bendamustine HCl monohydrate.

10. The formulation of claim 1, wherein the formulation contains no less than about 98% of the amount of the bendamustine active pharmaceutical ingredient upon analysis by HPLC after 6 months at room temperature.

11. The formulation of claim 10, wherein the formulation contains no less than about 98% of the amount of the bendamustine active pharmaceutical ingredient upon analysis by HPLC at initial testing and after 9 months at room temperature.

* * * * *